(12) United States Patent
Van Dun et al.

(10) Patent No.: US 9,518,270 B2
(45) Date of Patent: Dec. 13, 2016

(54) REVERSIBLE GENIC MALE STERILITY IN COMPOSITAE

(71) Applicant: RIJK ZWAAN ZAADTEELT EN ZAADHANDEL B.V., De Lier (NL)

(72) Inventors: Cornelis Maria Petrus Van Dun, Roosendaal (NL); Beatrice Ingrid Lindhout, Dordrecht (NL); Johannes Wilhelmus Schut, Wouw (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 399 days.

(21) Appl. No.: 13/785,084

(22) Filed: Mar. 5, 2013

(65) Prior Publication Data

US 2014/0201859 A1   Jul. 17, 2014

(30) Foreign Application Priority Data

Jan. 11, 2013   (EP) .................................. 13151073

(51) Int. Cl.
| | |
|---|---|
| *C12N 15/01* | (2006.01) |
| *A01H 1/06* | (2006.01) |
| *A01H 5/00* | (2006.01) |
| *C12N 15/82* | (2006.01) |
| *C07K 14/415* | (2006.01) |
| *C12N 9/02* | (2006.01) |
| *C12N 9/88* | (2006.01) |
| *C12N 9/90* | (2006.01) |
| *C12N 15/00* | (2006.01) |

(52) U.S. Cl.
CPC ......... *C12N 15/8289* (2013.01); *C07K 14/415* (2013.01); *C12N 9/0004* (2013.01); *C12N 9/88* (2013.01); *C12N 9/90* (2013.01); *C12N 15/8218* (2013.01); *A01H 1/06* (2013.01); *C12N 15/00* (2013.01)

(58) Field of Classification Search
None
See application file for complete search history.

(56) References Cited

U.S. PATENT DOCUMENTS

| | | | |
|---|---|---|---|
| 2003/0217388 A1* | 11/2003 | Feyereisen et al. | 800/286 |
| 2006/0150283 A1* | 7/2006 | Alexandrov et al. | 800/288 |
| 2006/0179498 A1* | 8/2006 | Dirks | A01H 1/00 800/14 |

OTHER PUBLICATIONS

Heffer et al, EvoDevo (2011) vol. 2 pp. 1-5.*
Sanders et al, Plant Cell (2000) 12: 1041-1061.*
Stintzi et al, Proceedings of the National Academy of Sciences of the United States of America (2000), 97: 10625-10630.*

* cited by examiner

*Primary Examiner* — Eileen B O Hara
*Assistant Examiner* — Stephen Uyeno
(74) *Attorney, Agent, or Firm* — Vedder Price P.C.; Thomas J. Kowalski; Deborah L. Lu

(57) ABSTRACT

The present invention relates to plants of the Compositae family exhibiting a reversible genic male sterility trait, characterized in that the genic male sterility may be caused by a reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase, or their functional homologs.

2 Claims, 2 Drawing Sheets

SEQUENCE LISTING

```
<160> NUMBER OF SEQ ID NOS: 2

<210> SEQ ID NO 1
<211> LENGTH: 1823
<212> TYPE: DNA
<213> ORGANISM: Lactuca sativa
<220> FEATURE:
<221> NAME/KEY: source
<222> LOCATION: 1..1823
<223> OTHER INFORMATION: /mol_type="DNA"
      /organism="Lactuca sativa"

<400> SEQUENCE: 1
atggctgaaa caccgccgtc tgccgacaat ccaactctct tttctccatt caagatgggc      60
aagtttaatc tctctcacag gtccgttgtt tctatccttt cttctcttca ctttctaatc     120
ataaatccgt cccccctata aaagtccttc agattttgag cttgatccag tcttgaccga     180
tcactatacc gtgttttggt tgtagggtgg tgttagctcc gatgacgcgg tgtagggcgt     240
taaatagcat accgaatcaa gctctggtgg agtattacag gcagagagca accgccggtg     300
ggtttctcat cacggagggg acaatgatct ctcctacctc cgccgggtaa tttcgctatt     360 cctttttgttc ttcaagggtg ttttagtaaa tcaacattcc aacataattc accgggacaa     420
accatataaa accgccacgt ggcaattctt agttccttac atagtgcttt gtgggacctg     480
cagtatagac tattattaaa gtcacaccat tattaaagtc acattctctt tataaccact     540
ttataaagtc tttataacta aaaatgtgt tttttcgtt gtactttata gttagattag     600
atgcataatg tggatcttat gaaccattaa acaatgatac aagctacttg tgttctaaag     660
ttaaagatgc cattttgatt cttaatttaa aaaacccatt tggtttagga atacccctt     720 attcatcgat cattataaag cccaaattaa cgatctttct ggtaaaaaaa aacccaattt     780
ggtgatcagg ttccctcacg taccaggtat atttaatcaa gaacaagttg aagcttggaa     840
gaaagtcgtg gatgcagttc atgaaaaagg cgctgtgatc ttttgttaat tatggcatgt     900
cggcagagca tcccaccaag gtacgctttc ttccatctaa aagtctcaaa atctcaacat     960
tttgattttt gaacctaaat tcgaatcgaa agtgatcatt gtgttgaaca aacagtatat    1020
caacctaatg gggttgcacc aatatcatct acaagcaaac ccatatcgaa aaaatggaga    1080
attttaatgc ccgatgggac ccacgctcaa tatccaaacc ctcgaccact cgctacccat    1140
gaaataccag aggtggtgga agactatcgt ctggcagcaa ttaacgccat tgaagcaggt    1200
tttgatggaa tcgagattca cggagcccat ggttatcttc tcgatcaatt catgaaagat    1260
ggcatcaata atcgaaccga tgaatatggt ggatctttag caaaccgatg caaattctta    1320
ctgaaagtgg tgaaatcgat agctacagcc attggtgcag ataaagtcgg tgttagaatc    1380
tcaccagcta ttgaccattt agacgccatg gattctgacc cacgtagctt agggcttgaa    1440
gtaattgaaa gactgaataa acttcaggtt gaattagggt caaagttgac ttatcttcat    1500
gtgactcaac caaggtacac ggcttatggt caaacagaag ctggaagcca tggaagtgaa    1560
gaggaagttg ctgagttgat gaagatatgg agaagggcat ttatgggaac ttttgtttgt    1620
agtggtgggt atactagaga gcttgggatt gaagctgtgg ctaaagggga tgctgatttg    1680
```

```
gtggcttatg gaaggctttt tatatcgaat ccggatttgg ttttgagact caaggttaat      1740
gcacctttga ataggtatgt tagggctagt ttttatacac atgatcctgt tgtagggtac      1800
actgattacc cttcacttga gaa                                              1823

<210> SEQ ID NO 2
<211> LENGTH: 289
<212> TYPE: DNA
<213> ORGANISM: Cichorium endivia
<220> FEATURE:
<221> NAME/KEY: source
<222> LOCATION: 1..289
<223> OTHER INFORMATION: /mol_type="DNA"
      /organism="Cichorium endivia"

<400> SEQUENCE: 2
tcaacatcca gatctccgat cccaagcaaa taatggctga aacgacgccg tctgccgaca        60
atccaaccct cttttctccg tacaagatgg gcaagttcaa tctctctcac agggtgatca       120
gttactttac ttcgatccat tgttctcgca gctttctgat catacttcat tcccccagca       180
aaataattca gaatttgacc ttgatccaat tctgttttta attcttttac cgattagttc       240
accgtgtttt ggttgtaggg tggtgttagc tcagatgacg agatgcagg                   289
```

REVERSIBLE GENIC MALE STERILITY IN COMPOSITAE

RELATED APPLICATIONS AND INCORPORATION BY REFERENCE

This application claims benefit of European patent application Serial No. 13151073.7 filed 11 Jan. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to Compositae plants exhibiting a reversible genic male sterility trait. The invention further relates to cells, seeds and progeny of such plants, and to propagation material for obtaining the plants. The invention also relates to markers and the use of the markers for identifying the presence of the reversible genic male sterility trait.

BACKGROUND OF THE INVENTION

In commercial plant breeding the production of hybrid seed is very important. Plants grown from hybrid seed are generally very uniform, and they benefit from heterosis (hybrid vigour), which can lead to a significant increase in yield and/or performance when compared to the parental lines of the hybrid, or to outcrossing (open-pollinated) lines. Typically the parental lines used for hybrid seed production are inbred, which implies that their genomes are largely homozygous. The combination of two largely homozygous genomes into a hybrid leads to a high degree of heterozygosity, if both parental lines were genetically unrelated or not closely related.

Efficient hybrid seed production in plant species that are able to self-fertilise requires adequate measures to prevent self-fertilisation of the plants on which hybrid seeds are to be produced. Various strategies have been developed to achieve this, and to obtain an efficient hybrid seed production setup. However, the complexity and amount of labour required for each of these strategies varies greatly.

A strategy that naturally occurs in certain plant species is the physical separation of male and female reproductive organs in separate flowers, either on separate plants (dioecious species) or on the same plant (monoecious species). This system naturally promotes outcrossing, and it can be easily taken advantage of for hybrid seed production.

Another natural strategy is self-incompatibility, which has e.g. been extensively studied in *Brassica* species. In this case, pollen is physically unable to fertilise egg cells from the same plant. The precise mechanism of the incompatibility interaction can differ. Either pollen hydration or germination is prevented, or pollen tube growth through the style is inhibited by the female tissues, or the pollen tube is not attracted to ripe ovules, or the sperm nuclei are unable to merge with the egg cell nucleus to form a viable zygote. Again, this naturally occurring system is very efficient and useful for preventing self-fertilisation, and for promoting outcrossing.

Another method for preventing selfing, which is typically used in e.g. maize, is the mechanical elimination of all male flowers (detasseling). The only flowers remaining on the plant are female, and these can be manually pollinated with pollen from a selected paternal line, in order to obtain ears with exclusively hybrid kernels.

In plant species with hermaphroditic flowers (producing both ovules and pollen grains within the same flower), a common strategy for preventing selfing is emasculation by mechanical removal of anthers and/or pollen prior to anthesis. When the anthers are mechanically removed before the pollen grains are released from the loculi and/or before the filament has extended far enough to match the height of the stigma, selfing is efficiently prevented. Subsequently the female reproductive parts of the emasculated flower are allowed to mature normally, after which pollen grains from a selected father plant can be deposited on the stigma, in order to obtain exclusively hybrid seeds from the cross. Especially for commercial-scale applications this method is however very labour-intensive and not 100% reliable: if anthers are removed in a slightly too late developmental stadium or if one anther is accidentally not removed, this can lead to a mixed seed set, consisting of hybrid and maternal seeds. This results in non-uniformity of the commercial seed batch, which is undesired for customers who expect uniform and consistently superior seeds, and it brings inbred mother lines of hybrid varieties into commerce, which is undesired for the breeding company. A 100% reliable hybrid system is therefore desirable.

Another approach is to induce male sterility by means of chemicals. This so-called male gametocide can be achieved by treatment with e.g. gibberellins (in rice and maize), sodium methyl arsenate (in rice), or maleic acid (in wheat and onion). Disadvantages of this approach are the fact that this male sterility is not inheritable as it does not result from a genetic determinant present in the plant's genome, and that chemical treatment is labour intensive and not 100% reliable.

Another category of mechanisms through which selfing can be prevented, is termed genetic male sterility. Here three different approaches can be distinguished: genetic-engineered male sterility (transgenic MS), cytoplasmic male sterility (CMS) and genic male sterility (GMS). Transgenic MS comprises all approaches that use a transgene to ensure that pollen grains are unable to fertilise ovules, and that either lead to the death of pollen grains prior to anthesis, or to the dysfunctionality of pollen grains at anthesis. A well-known example is the reversible Barnase/Barstar system, wherein the Barnase enzyme is transgenically expressed in the tapetum, which leads to pollen sterility. However, when the Barstar protein is co-expressed in the tapetum, it blocks Barnase activity and restores pollen fertility (Mariani et al., 1990, *Nature* 347: 737-41).

Cytoplasmic male sterility (CMS) is a type of sterility that is under control of extra-nuclear, cytoplasmic factors, more precisely of plastid origin. Usually mutations in the mitochondrial genome underlie CMS, and they typically inherit in a maternal fashion. Routine hybrid seed production with CMS lines requires the use of maintainer and restorer lines, which complicates the process and increases the costs and time required for commercial hybrid seed production.

Genic male sterility (GMS) encompasses a nuclear influence on male fertility, in contrast to cytoplasmic influences which are caused by organellar factors. Due to e.g. a mutation in a nuclear gene the plant does not produce viable and/or functional pollen grains or male spores, and/or it is unable to disperse its pollen due to e.g. non-dehiscence of its anthers.

The Asteraceae family—also known as the Compositae family—is one of the largest extant plant families. It comprises various commercially important crop plants, such as sunflower (*Helianthus*), lettuce (*Lactuca*), endive, witloof and radicchio (*Cichorium*), artichoke (*Cynara*), and many ornamental plants such as *Chrysanthemum, Tagetes, Gerbera* and *Zinnia*.

In the Compositae family only few types of male sterility have been developed for commercial exploitation and hybrid seed production. Emasculation is very difficult in this family, due to the composite nature of the inflorescences. In e.g. endive and witloof, self-pollination is normally prevented by spraying an inflorescence with water, to flush away the pollen. Timing is crucial, because this spraying needs to be done immediately after opening of the anthers, before the stigma splits into two curving parts that protrude beyond the anthers. After spraying the inflorescence has to be blown dry and has to be allowed to develop further, before pollen grains from a selected father can be deposited onto the stigma. It is critical to choose the optimal moment for spraying with water: if pollen are removed too late some self-pollination will already have occurred, and if pollen are removed before the anthers are fully opened, pollen grains will remain present and may cause self-pollination at a later stage. Every day there is only a limited time window during which this spraying can be done, and its timing depends strongly on light and temperature conditions. The development of an efficient, reversible male sterility system in the Compositae family would thus greatly facilitate breeding in crop species belonging to this family.

Hybrid sunflowers are available and can be produced using various methods described above. However for e.g. endive a hybrid system is not yet available at all, and a major problem is the very limited genetic variation within this cultivated crop. If an efficient hybrid system would be available for endive, this could be used to increase the genetic variation, as well as provide additional benefits through heterotic effects. Interspecific crosses with e.g. witloof (*Cichorium intybus*) are possible, and these could be used to introduce foreign genetic material into endive germplasm, but this would lead to complications at the genetic level, namely the fact that the resulting progeny would no longer be purely endive, but a mixture of endive and witloof.

In witloof a recessive GMS trait has previously been created through a transposon insertion in a homologue of the DYT1 gene of *Arabidopsis* (Quillet et al., 2011, Cloning and characterization of nuclear male sterility 1 (nms1) in chicory. However, in practice it is very difficult to transfer this transposon-based trait to endive (*Cichorium endivia*). Also, although the transposon may spontaneously be excised from the DYT1 gene homologue and thus potentially restore fertility, a researcher is not able to easily, predictably and consistently reverse this male sterility trait in witloof whenever he wishes to do so.

CMS has also been created in witloof, by combining the nuclear genome from *C. intybus* with cytoplasm from sunflower (*Helianthus annuus*). However, again this is not a reversible male sterility, and the perpetuation of the trait requires maintainer and restorer lines.

In lettuce, male sterility has been described in the prior art, and pollination for obtaining hybrid seeds can e.g. be achieved with bees (U.S. Pat. No. 7,569,743). Dominant GMS is available (resulting from the MS7 mutation), as well as CMS (through combination of the nuclear genome of *Lactuca sativa* with the cytoplasm of sunflower). However, none of these traits is reversible, and it thus requires more efforts to maintain the male sterile mother lines in any of those cases.

One could imagine a transgenic approach to obtain reversible male sterility in Compositae plants, e.g. with the Barnase/Barstar system, but such transgenic plants would have a "regulated" status, which is undesired in e.g. the European market, and this would necessitate large extra deregulation expenses to obtain market approval. The cost for bringing hybrid seeds resulting from the use of such a transgenic reversible male-sterile Compositae plant to the market would thus become quite high.

Citation or identification of any document in this application is not an admission that such document is available as prior art to the present invention.

SUMMARY OF THE INVENTION

It is therefore an object of the present invention to provide a reversible male sterility system in Compositae plants for the efficient and convenient production of hybrid seeds.

In the research leading to the present invention it was found that Compositae plants may be rendered male-sterile through a loss-of-function mutation in the OPR3 gene, and that this male sterility may be reversed by the application of methyl jasmonate (MeJA) and/or jasmonic acid or other jasmonic acid derivatives to flower buds.

The OPR3 gene encodes the 12-oxophytodienoic acid reductase protein, which is a key enzyme in the biosynthesis of the phytohormone jasmonic acid. In the model plant species *Arabidopsis thaliana* jasmonic acid is required for male fertility, and mutations in the *Arabidopsis* OPR3 gene were reported to cause male sterility. Male fertility could be restored by treating flower buds with methyl jasmonate (Stintzi and Browse, 2000; *Proc. Natl. Acad. Sci. USA* 97: 10625-10630). However, this observation in *Arabidopsis* is apparently not by definition valid for other plant species. In tomato, for example, jasmonic acid is required for the maternal control of seed maturation, but not for male fertility (Li et al., 2004; *Plant Cell* 16: 126-143). This indicates that the jasmonic acid pathway regulates distinct developmental processes in different plant species.

It is surprising that targeting functional homologues of the OPR3 gene in a plant family other than the Brassicaceae actually leads to reversible male sterility, especially since from a phylogenetic point of view the Compositae family is closer related to the Solanaceae family (comprising tomato, in which jasmonic acid is not involved in male fertility) than to the Brassicaceae family (comprising *Arabidopsis*). Among the eudicots, the Compositae and Solanaceae families both belong to the Asterids Glade, whereas the Brassicaceae family belongs to the Rosids Glade. The skilled person would not be able to establish, without undue burden, in which plant families other than the Brassicaceae or Solanaceae, which have been investigated in the prior art, the jasmonic acid pathway may or may not regulate male fertility.

Reversible genic male sterility provides a great advantage over non-reversible genic male sterility. When the genic male sterility trait performs in a reliable and consistent manner, a male-sterile mother plant will exclusively produce hybrid seeds, when pollinated with pollen from a selected father plant (e.g. through manual pollination or insect pollination), without a need for emasculation or other means to induce male sterility. In addition, it is very easy to propagate and maintain the male sterile mother plant: upon a specific treatment, the male sterility may be reversed and the mother plant becomes entirely fertile, and it may thus self-fertilise to produce inbred seeds that are homozygous for the said genic male sterility trait. In cases of non-reversible genic male sterility this is not possible, and it is more difficult to maintain the genic male sterility trait from generation to generation.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with NCIMB, under deposit accession numbers 42060 and 42092 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
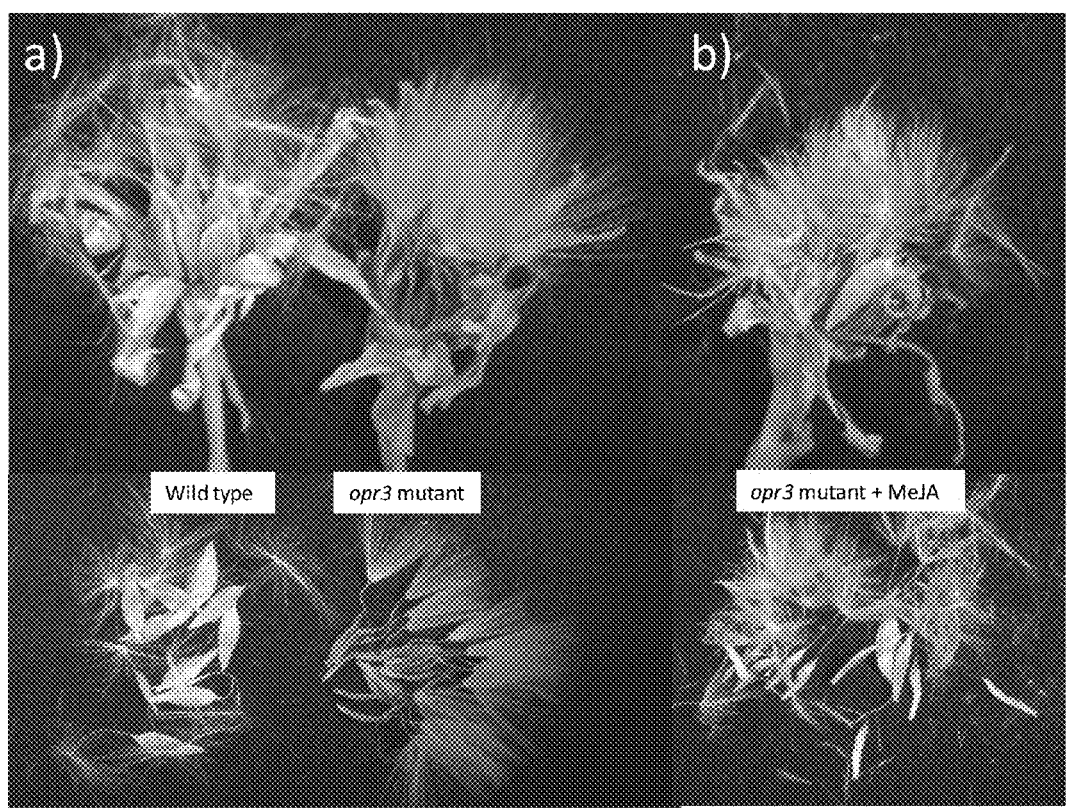
FIG. 1: Reversible male sterility in lettuce Panel A shows an inflorescence from a wild-type lettuce plant after flowering (left-hand side), as compared to an inflorescence from a lettuce plant of the invention after flowering (right-hand side). Neither of the plants has been pollinated with pollen from another lettuce plant. The wild-type lettuce plant is fully fertile, and it has produced seeds through selfing. The lettuce plant of the invention, in contrast, which has not been treated with jasmonic acid and/or one or more jasmonic acid derivatives, shows a complete absence of seeds in the inflorescence. This demonstrates that the presence of the reversible genic male sterility trait of the invention makes the plant completely self-sterile. Panel B illustrates the effect of treatment with jasmonic acid and/or jasmonic acid derivatives on the fertility of a reversible genic male sterile lettuce plant of the invention. The inflorescence was treated with methyl jasmonate ("MeJA") during its development, and has produced seeds through selfing.

This invention relates to a plant of the Compositae family (also known as the Asteraceae family) exhibiting a reversible genic male sterility trait, characterised in that the genic male sterility trait is caused by the reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase, or their functional homologues.

The aforementioned genes encode the enzymes that constitute the jasmonic acid biosynthetic pathway in plants. Lipoxygenase converts α-linolenic acid to 13-hydroperoxylinoleic acid, which is further converted to 12,13-epoxyoctadecatrienoic acid by the action of allene oxide synthase. The latter molecule is the substrate of allene oxide cyclase, by which it is converted into (9S,13S)-12-oxo-phytodienoic acid, which may be further processed into 3-oxo-2(2'[Z]-pentenyl)-cyclopentane-1-octanoic acid by the enzymatic action of the 12-oxo-phytodienoic acid-10,11-reductase (OPR3) enzyme. Three cycles of β-oxidation are subsequently required to convert the 3-oxo-2(2'[Z]-pentenyl)-cyclopentane-1-octanoic acid molecule into (3R, 7S)-jasmonic acid.

In one embodiment the male sterility in plants of the invention may be reversed by the application of one or more jasmonic acid derivatives, in particular methyl jasmonate. Methyl jasmonate (MeJA) is a volatile derivative of jasmonic acid from which it may be converted in planta in a reaction catalysed by the S-adenosyl-L-methionine:jasmonic acid carboxyl methyltransferase enzyme.

In another embodiment jasmonic acid may be used.

Conditional and controlled reversibility of the male sterility phenotype is very useful, because it allows the easy maintenance of male sterile plants of the invention across successive generations. The application of one or more jasmonic acid derivatives, in particular methyl jasmonate, renders the male sterile plants of the invention entirely fertile (both male- and female-fertile), and capable of self-fertilisation. In this manner the male sterility trait of the invention may be conveniently transmitted to the next generation, without the need for e.g. restorer or maintainer lines.

The application of jasmonic acid and/or one or more jasmonic acid derivatives, in particular methyl jasmonate, may be done in various ways, such as spraying them in an aqueous solution or directly applying them with a brush onto young flower buds in an aqueous solution, or on a regular basis adding them to the water or substrate provided to the plants, such that they are taken up by the plant and distributed therein in a systemic manner.

In one embodiment the interfering with the one or more target genes involved in endogenous jasmonic acid production consists of preventing transcription thereof. Preventing transcription may for example be achieved by means of RNA oligonucleotides, DNA oligonucleotides or RNAi molecules directed against the target gene promoter, or preferably by means of the expression of a negatively acting transcription factor acting on the target gene promoter.

In another embodiment the interfering with the one or more target genes involved in endogenous jasmonic acid production consists of destabilising the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides.

In another embodiment the interfering with the one or more target genes involved in endogenous jasmonic acid production consists of inhibiting the target gene expression product, preferably by means of the expression product(s) of one or more dominant negative nucleic acid constructs, or preferably by means of one or more chemical compounds.

In yet another embodiment the interfering with the one or more target genes involved in endogenous jasmonic acid production consists of the introduction of one or more mutations into the target gene, leading to perturbation of its biological function. The one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements. The one or more mutations may also be introduced specifically by means of homologous recombination or oligonucleotide-based mutation induction.

This invention also relates to plants of the genus *Lactuca*, exhibiting a reversible genic male sterility trait according to the present invention. In one embodiment, the plants belong to the species *Lactuca sativa*, and the reversible male sterility trait is caused by a genetic determinant, the presence of which genetic determinant may be identified by a molecular marker characterised by SEQ ID No. 1, and wherein the said genetic determinant is as present in the genome of plants grown from seed of which a representative sample was deposited with the NCIMB under accession number NCIMB 42060.

This invention also relates to *Lactuca* plants exhibiting a reversible genic male sterility trait, obtainable by crossing a first *Lactuca* plant with a second *Lactuca* plant, wherein one of the said plants is grown from seeds of which a representative sample was deposited with the NCIMB under accession number NCIMB 42060, or a progeny plant thereof, and selecting, preferably in the F2 generation, for plants that exhibit a reversible genic male sterility trait.

Alternatively, selection may already be done in the F1 generation by means of a molecular marker detecting the SNP of SEQ ID No. 1.

This invention further relates to seed of a *Lactuca* plant exhibiting a reversible genic male sterility trait, wherein the plant that may be grown from the seed may comprise the genetic determinant that may be identified by a molecular marker characterised by SEQ ID No. 1, and wherein the said genetic determinant is as present in the genome of plants grown from seed of which a representative sample was deposited under accession number NCIMB 42060.

This invention further relates to progeny of a *Lactuca* plant exhibiting a reversible genic male sterility trait, which may comprise the genetic determinant that may be identified by a molecular marker characterised by SEQ ID No. 1, and wherein the said genetic determinant is as present in the genome of plants grown from seed of which a representative sample was deposited under accession number NCIMB 42060.

Such progeny may be produced by sexual or vegetative reproduction of a plant of the invention or a progeny plant thereof. The progeny plant displays the reversible genic male sterility trait in the same or in a similar way as the plant of which representative seed was deposited under accession number NCIMB 42060. This means that such progeny has the same characteristics as claimed for lettuce plants of the invention.

As used herein, the word "progeny" is intended to mean the offspring or the first and all further descendants from a cross with a plant of the invention that shows the reversible genic male sterility trait. Progeny of the invention may comprise descendants of any cross with a plant of the invention that carries the reversible genic male sterility trait. Such progeny is for example obtainable by crossing a first lettuce plant with a second lettuce plant, wherein one of the lettuce plants was grown from seeds of a plant of the invention, representative seeds of which were deposited under NCIMB accession number 42060, but it may also be the progeny of any other lettuce plant carrying the reversible genic male sterility trait as present in seeds of deposit NCIMB 42060.

It is understood that a parent plant that provides the trait of the invention is not necessarily a plant grown directly from the deposited seeds. The parent may also be a progeny plant from the seed, or a progeny plant from seeds that are identified to have (or to have acquired) the trait of the invention by other means. In one embodiment, the invention relates to lettuce plants that carry the trait of the invention and that have acquired the said trait by introduction of the genetic information that is responsible for the trait from a suitable source, either by conventional breeding, or genetic modification, in particular by cis-genesis or transgenesis. Cis-genesis is genetic modification of plants with a natural gene, encoding an (agricultural) trait from the crop plant itself or from a sexually compatible donor plant. Transgenesis is genetic modification of a plant with a gene from a non-crossable species or with a synthetic gene.

In one embodiment, the source from which the genetic information is acquired is formed by plants grown from the deposited seeds, or by sexual or vegetative descendants therefrom.

"Progeny" also encompasses plants that carry the trait of the invention which are obtained from other plants of the invention by vegetative propagation or multiplication.

This invention also relates to propagation material suitable for producing a *Lactuca* plant exhibiting a reversible genic male sterility trait, which may comprise the genetic determinant that may be identified by a molecular marker characterised by SEQ ID No. 1, and wherein the said genetic determinant is as present in the genome of plants grown from seed of which a representative sample was deposited under accession number NCIMB 42060.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a lettuce plant grown or regenerated from the said propagation material of a plant of the invention, which plant exhibits the reversible genic male sterility trait of the invention.

The invention further relates to a cell of a lettuce plant of the invention, which cell may comprise a genetic determinant which leads to reversible genic male sterility, wherein the said genetic determinant is as present in a lettuce plant, representative seeds of which were deposited under NCIMB accession number 42060. The said cell thus may comprise the genetic information encoding the said reversible genic male sterility trait, in particular genetic information which is substantially identical, preferably completely identical to the genetic information encoding the said reversible genic male sterility trait of the lettuce plant, representative seeds of which were deposited under NCIMB accession number 42060. Preferably, the cell of the invention is part of a plant or plant part, but the cell may also be in isolated form.

The invention also relates to a cell of a lettuce plant of the invention, which cell may comprise a genetic determinant which leads to reversible genic male sterility, and which plant is obtained by transferring the reversible genic male sterility trait as found in seeds that were deposited under NCIMB accession number 42060 into an agronomically valuable lettuce plant.

The invention further relates to seed of the lettuce plant of the invention, which seed contain in their genome the genetic information that encodes the reversible genic male sterility trait of the invention.

The invention also relates to the use of seeds that were deposited under NCIMB accession number 42060 for transferring reversible genic male sterility into another agronomically valuable lettuce plant.

The invention also relates to the use of a lettuce plant of the invention that exhibits reversible genic male sterility due to the presence, in the genome of the plant, of the reversible genic male sterility trait as found in seeds that were deposited under NCIMB accession number 42060 as a crop.

The invention further relates to the use of a lettuce plant of the invention that exhibits reversible genic male sterility due to the presence, in the genome of the plant, of the reversible genic male sterility trait as found in seeds that were deposited under NCIMB accession number 42060 as a source of seed.

The invention also relates to the use of a lettuce plant of the invention that exhibits reversible genic male sterility due to the presence, in the genome of the plant, of the reversible genic male sterility trait as found in seeds that were deposited under NCIMB accession number 42060 as a source of propagating material.

The invention also relates to the use of a lettuce plant of the invention that exhibits reversible genic male sterility due to the presence, in the genome of the plant, of the reversible genic male sterility trait as found in seeds that were deposited under NCIMB accession number 42060 for consumption.

The invention also relates to harvested leaves of lettuce plants of the invention, to food products which may comprise harvested leaves of lettuce plants of the invention, either in natural or in processed form, and to a container which may comprise one or more lettuce plants of the invention in a growth substrate for harvest of leaves from the lettuce plant in a domestic environment.

The invention further relates to the use of a lettuce plant of the invention in breeding to confer reversible genic male sterility.

The invention also relates to the use of the reversible genic male sterility trait as found in seeds that were deposited under NCIMB accession number 42060 for conferring reversible genic male sterility onto a *Lactuca sativa* plant.

The invention further relates to the use of a *Lactuca sativa* plant as a recipient of the reversible genic male sterility trait as found in seeds that were deposited under NCIMB accession number 42060.

In one aspect the invention relates to a method for production of a *Lactuca sativa* plant which exhibits a reversible genic male sterility trait, which may comprise
  a) crossing a plant which may comprise a genetic determinant that leads to the trait with another plant;
  b) selfing the resulting F1 for obtaining F2 plants;
  c) selecting plants that have the trait in the F2;
  d) optionally performing one or more additional rounds of selfing or crossing, and subsequently selecting for a plant which may comprise/showing the trait of the invention.

In one aspect, the invention relates to a method for production of a *Lactuca sativa* plant which exhibits a reversible genic male sterility trait, which may comprise
  a) crossing a plant which may comprise the genetic determinant that leads to the trait with another plant;
  b) optionally backcrossing the resulting F1 with the preferred parent;
  c) selecting for plants that have the trait in the F2;
  d) optionally performing one or more additional rounds of selfing or crossing, and subsequently selecting for a plant which may comprise the trait.

The invention additionally provides a method of introducing another desired trait into a *Lactuca sativa* plant which exhibits the reversible genic male sterility trait, which may comprise:
  a) crossing a *Lactuca sativa* plant that exhibits the reversible genic male sterility trait, representative seed of which were deposited under deposit number NCIMB 42060, with a second *Lactuca sativa* plant that may comprise a desired trait to produce F1 progeny;
  b) selecting an F1 progeny that may comprise said reversible genic male sterility trait and the desired trait;
  c) crossing the selected F1 progeny with either parent, to produce backcross progeny;

d) selecting backcross progeny which may comprise the desired trait and the reversible genic male sterility trait; and e) optionally repeating steps c) and d) one or more times in succession to produce selected fourth or higher backcross progeny that may comprise the desired trait and the reversible genic male sterility trait. The invention includes a *Lactuca sativa* plant produced by this method.

In one embodiment selection for plants exhibiting the reversible genic male sterility trait is done in the F1 or any further generation by using a molecular marker characterised by SEQ ID No. 1. In another aspect selection for the trait of the invention is started in the F2 of a cross or alternatively of a backcross. Selection of plants in the F2 may be done phenotypically as well as by using the said marker which directly or indirectly detects the genetic determinant underlying the trait.

In one embodiment selection for plants exhibiting the reversible genic male sterility trait is started in the F3 or a later generation.

In one embodiment the plant which may comprise the genetic determinant is a plant of an inbred line, a hybrid, a doubled haploid, or of a segregating population.

The invention further provides a method for the production of a *Lactuca sativa* plant exhibiting the reversible genic male sterility trait by using a doubled haploid generation technique to generate a doubled haploid line which may comprise the said trait.

The invention also relates to a method for the production of a *Lactuca sativa* plant exhibiting the reversible genic male sterility trait by using a seed that may comprise a genetic determinant in its genome that leads to the reversible genic male sterility trait for growing the said *Lactuca sativa* plant. The seeds are suitably seeds of which a representative sample was deposited under deposit number NCIMB 42060.

The invention also relates to a method for seed production which may comprise growing *Lactuca sativa* plants from seeds of which a representative sample was deposited under deposit accession number NCIMB 42060, reversing the reversible genic male sterility by the application of jasmonic acid and/or one or more jasmonic acid derivatives, in particular methyl jasmonate, allowing the plants to produce seeds, and harvesting those seeds. Production of the seeds is suitably done by crossing or selfing. Crossing may e.g. be done by means of hand pollination or by employing suitable pollinating insects.

In one embodiment, the invention relates to a method for the production of a *Lactuca sativa* plant exhibiting the reversible genic male sterility trait by using tissue culture.

The invention furthermore relates to a method for the production of a *Lactuca sativa* plant exhibiting the reversible genic male sterility trait by using vegetative reproduction.

In one embodiment, the invention relates to a method for the production of a *Lactuca sativa* plant exhibiting the reversible genic male sterility trait by using a method for genetic modification to introduce in particular dominantly acting transgenes that cause the said trait into the *Lactuca sativa* plant, for example by means of RNAi, amiRNA or antisense, or dominant-negative versions of a target gene, or through mutation. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. The plant may also be genetically modified by mutation of a target gene to exhibit the male sterility trait of the invention.

The invention also relates to a breeding method for the development of *Lactuca sativa* plants that exhibit the reversible genic male sterility trait wherein germplasm which may comprise said trait is used. Representative seed of said plant which may comprise the genetic determinant and being representative for the germplasm was deposited under deposit accession number NCIMB 42060.

In a further embodiment the invention relates to a method for the production of a *Lactuca sativa* plant exhibiting the reversible genic male sterility trait wherein progeny or propagation material of a plant which may comprise the genetic determinant conferring said trait is used as a source to introgress the said trait into another *Lactuca sativa* plant. Representative seed of said plant which may comprise the genetic determinant was deposited under deposit accession number NCIMB 42060.

The invention provides preferably a *Lactuca sativa* plant exhibiting the reversible genic male sterility trait, which plant is obtainable by any of the methods herein described and/or familiar to the skilled person.

This invention also relates to the use of *Lactuca sativa* plants exhibiting a reversible genic male sterility trait as a female parent for the creation of hybrid *Lactuca sativa* seeds. The fact that *Lactuca sativa* plants of the invention are unable to self-fertilise due to male sterility (if they are not rendered male fertile by the application of one or more jasmonic acid derivatives, in particular methyl jasmonate) makes it possible to efficiently use *Lactuca sativa* plants of the invention as female parents for the efficient creation of hybrid *Lactuca sativa* plants, using pollen from other *Lactuca sativa* plants. Pollination of the plants of the invention may e.g. be achieved by means of manual pollination, or by employing suitable pollinating insects, such as bumblebees, bees or flies and placing reversible genic male sterile *Lactuca sativa* plants of the invention alongside male-fertile *Lactuca sativa* plants that will function as father plants of the hybrid *Lactuca sativa* seeds, by providing functional pollen grains for a successful fertilisation of the reversible genic male sterile *Lactuca sativa* plants of the invention. This invention further relates to hybrid lettuce seeds, obtainable by the use of *Lactuca sativa* plants exhibiting a reversible genic male sterility trait as a female parent.

According to a further aspect thereof the invention also relates to plants of the genus *Cichorium*, exhibiting the reversible genic male sterility trait. The genus *Cichorium* may comprise economically and agriculturally relevant crop species, such as *Cichorium endivia* (endive) and *Cichorium intybus* (witloof, radicchio), and also *Cichorium spinosum* and *Cichorium pumillum*, which may all be crossed to each other.

In one embodiment, the said plants belong to the genus *Cichorium* and in particular to the species *Cichorium endivia*, and the reversible male sterility trait is caused by a genetic determinant, which is as present in the genome of plants grown from seed of which a representative sample was deposited under accession number NCIMB 42092, in which the presence of the genetic determinant may be identified by a molecular marker characterised by SEQ ID No. 2.

This invention also relates to *Cichorium* plants, in particular *Cichorium endivia* plants, exhibiting a reversible genic male sterility trait, obtainable by crossing a first *Cichorium* plant, in particular a *Cichorium endivia* plant, with a second *Cichorium* plant, in particular a *Cichorium endivia* plant, wherein one of the said plants is grown from seeds of which a representative sample was deposited with the NCIMB under accession number NCIMB 42092, or a progeny plant thereof, and selecting, preferably in the F2 generation, for plants that exhibit a reversible genic male sterility trait.

This invention further relates to seed of a *Cichorium* plant, in particular a *Cichorium endivia* plant exhibiting a reversible genic male sterility trait, which is as present in the genome of plants grown from seed of which a representative sample was deposited under accession number NCIMB 42092, in which the presence of the genetic determinant may be identified by a molecular marker characterised by SEQ ID No. 2.

This invention further relates to progeny of a *Cichorium* plant, in particular a *Cichorium endivia* plant, exhibiting a reversible genic male sterility trait, which may comprise the genetic determinant, which is as present in the genome of plants grown from seed of which a representative sample was deposited under accession number NCIMB 42092, in which the presence of the genetic determinant may be identified by a molecular marker characterised by SEQ ID No. 2.

Such progeny may be produced by sexual or vegetative reproduction of a plant of the invention or a progeny plant thereof. The progeny plant displays the reversible genic male sterility trait in the same or in a similar way as the plant of which representative seed was deposited (NCIMB 42092). This means that such progeny has the same characteristics as claimed for endive plants of the invention.

As used herein the word "progeny" is intended to mean the offspring or the first and all further descendants from a cross with a plant of the invention that shows the reversible genic male sterility trait. Progeny of the invention may comprise descendants of any cross with a plant of the invention that carries the reversible genic male sterility trait. Such progeny is for example obtainable by crossing a first endive plant with a second endive plant, wherein one of the endive plants was grown from seeds of a plant of the invention, representative seeds of which were deposited under NCIMB accession number 42092, but it may also be the progeny of any other endive plant or another *Cichorium* plant carrying the reversible genic male sterility trait as present in NCIMB 42092.

It is to be understood that a parent plant that provides the trait of the invention is not necessarily a plant grown directly from the deposited seeds. The parent may also be a progeny plant from the seed, or a progeny plant from seeds that are identified to have (or to have acquired) the trait of the invention by other means. In one embodiment, the invention relates to endive plants that carry the trait of the invention and that have acquired the said trait by introduction of the genetic information that is responsible for the trait from a suitable source, either by conventional breeding, or genetic modification, in particular by cis-genesis or transgenesis. Cis-genesis is genetic modification of plants with a natural gene, encoding an (agricultural) trait from the crop plant itself or from a sexually compatible donor plant. Transgenesis is genetic modification of a plant with a gene from a non-crossable species or with a synthetic gene.

In one embodiment, the source from which the genetic information is acquired is formed by plants grown from the deposited seeds, or by sexual or vegetative descendants therefrom. "Progeny" also encompasses plants that carry the trait of the invention which are obtained from other plants of the invention by vegetative propagation or multiplication.

This invention also relates to propagation material suitable for producing a *Cichorium* plant, in particular a *Cichorium endivia* plant exhibiting a reversible genic male sterility trait, which may comprise a genetic determinant which is as present in the genome of plants grown from seed of which a representative sample was deposited under accession number NCIMB 42092, in which the genetic determinant may be identified by a molecular marker characterised by SEQ ID No. 2.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a *Cichorium* plant grown or regenerated from the said propagation material of a plant of the invention, which plant exhibiting the reversible genic male sterility trait of the invention.

The invention further relates to a cell of an endive plant of the invention, which cell may comprise a genetic determinant which leads to reversible genic male sterility, wherein the said genetic determinant is as present in an endive plant, representative seeds of which were deposited under NCIMB accession number 42092, in which the genetic determinant may be identified by a molecular marker characterised by SEQ ID No. 2. The said cell thus may comprise the genetic information encoding the said reversible genic male sterility trait, in particular genetic information which is substantially identical, preferably completely identical to the genetic information encoding the said reversible genic male sterility trait of the endive plant, representative seeds of which were deposited under NCIMB accession number 42092, in which the genetic determinant may be identified by a molecular marker characterised by SEQ ID No. 2. Preferably, the cell of the invention is part of a plant or plant part, but the cell may also be in isolated form.

The invention also relates to a cell of a *Cichorium* plant, in particular a *Cichorium endivia* plant of the invention, which cell may comprise a genetic determinant which leads to reversible genic male sterility, and which plant is obtained by transferring the reversible genic male sterility trait as found in seeds that were deposited under NCIMB accession number 42092 into an agronomically valuable endive plant.

The invention further relates to seed of a *Cichorium* plant, in particular a *Cichorium endivia* plant of the invention, which seed contain in their genome the genetic information that encodes the reversible genic male sterility trait of the invention.

The invention also relates to the use of seeds that were deposited under NCIMB accession number 42092 for transferring reversible genic male sterility into another agronomically valuable endive plant.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a crop.

The invention further relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a source of seed.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a source of propagating material.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 for consumption.

The invention also relates to harvested leaves of a *Cichorium* plant, in particular a *Cichorium endivia* plant of the invention, to food products which may comprise harvested leaves of endive plants of the invention, either in natural or in processed form, and to a container which may comprise one or more endive plants of the invention in a growth substrate for harvest of leaves from the endive plant in a domestic environment.

The invention further relates to the use of a *Cichorium* plant, in particular a *Cichorium endivia* plant of the invention in breeding to confer reversible genic male sterility.

The invention also relates to the use of the reversible genic male sterility trait as found in seeds that were deposited under NCIMB accession number 42092 for conferring reversible genic male sterility onto a *Cichorium endivia* plant.

The invention further relates to the use of a *Cichorium* plant as a recipient of the reversible genic male sterility trait as found in seeds that were deposited under NCIMB accession number 42092, in which the genetic determinant may be identified by a molecular marker characterised by SEQ ID No. 2.

In one aspect the invention relates to a method for production of a *Cichorium* plant, in particular a *Cichorium endivia* plant which exhibits a reversible genic male sterility trait, which may comprise
   a) crossing a plant which may comprise a genetic determinant that leads to the trait with another plant;
   b) selfing the resulting F1 for obtaining F2 plants;
   c) selecting plants that have the trait in the F2;
   d) optionally performing one or more additional rounds of selfing or crossing, and subsequently selecting for a plant which may comprise/showing the trait of the invention.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a *Cichorium* plant, in particular a *Cichorium endivia* plant, which exhibits a reversible genic male sterility trait, which may comprise
   a) crossing a plant which may comprise the genetic determinant that leads to the trait with another plant;
   b) optionally backcrossing the resulting F1 with the preferred parent;
   c) selecting for plants that have the trait in the F2;
   d) optionally performing one or more additional rounds of selfing or crossing, and subsequently selecting for a plant which may comprise the trait.

The invention additionally provides a method of introducing another desired trait into a *Cichorium* plant, in particular a *Cichorium endivia* plant, which exhibits the reversible genic male sterility trait, which may comprise:
   a) crossing a *Cichorium* plant, in particular a *Cichorium endivia* plant, that exhibits the reversible genic male sterility trait, representative seed of which were deposited under deposit number NCIMB 42092, with a second *Cichorium* plant, in particular a *Cichorium endivia* plant, that may comprise a desired trait to produce F1 progeny;
   b) selecting an F1 progeny that may comprise said reversible genic male sterility trait and the desired trait;
   c) crossing the selected F1 progeny with either parent, to produce backcross progeny;
   d) selecting backcross progeny which may comprise the desired trait and the reversible genic male sterility trait; and
   e) optionally repeating steps c) and d) one or more times in succession to produce selected fourth or higher backcross progeny that may comprise the desired trait and the reversible genic male sterility trait. The invention includes a *Cichorium* plant, in particular a *Cichorium endivia* plant, produced by this method.

In one embodiment selection for plants exhibiting the reversible genic male sterility trait is done in the F1 or any further generation by using a molecular marker characterised by SEQ ID No. 2. In another aspect selection for the trait of the invention is started in the F2 of a cross or alternatively of a backcross. Selection of plants in the F2 may be done phenotypically as well as by using the said marker which directly or indirectly detects the genetic determinant underlying the trait.

Phenotypic selection may be done based on the observation of male sterility (whereby only non-functional pollen grains are formed) and/or based on the observation of flower colour. When the genetic determinant underlying the trait of the invention is present in a homozygous state, this correlates with a pale flower colour, when compared to plants not having the said genetic determinant, or to plants in which the said genetic determinant is present in a heterozygous state.

In one embodiment selection for plants exhibiting the reversible genic male sterility trait is started in the F3 or a later generation.

In one embodiment the plant which may comprise the genetic determinant is a plant of an inbred line, a hybrid, a doubled haploid, or of a segregating population.

The invention further provides a method for the production of a *Cichorium* plant, in particular a *Cichorium endivia* plant, exhibiting the reversible genic male sterility trait by using a doubled haploid generation technique to generate a doubled haploid line which may comprise the said trait.

The invention also relates to a method for the production of a *Cichorium* plant, in particular a *Cichorium endivia* plant, exhibiting the reversible genic male sterility trait by using a seed that may comprise a genetic determinant in its genome that leads to the reversible genic male sterility trait for growing the said a *Cichorium* plant, in particular a *Cichorium endivia* plant. The seeds are suitably seeds of which a representative sample was deposited with the NCIMB under deposit number NCIMB 42092.

The invention also relates to a method for seed production which may comprise growing *Cichorium endivia* plants from seeds of which a representative sample was deposited under deposit number NCIMB 42092, reversing the reversible genic male sterility by the application of jasmonic acid and/or one or more jasmonic acid derivatives, in particular methyl jasmonate, allowing the plants to produce seeds, and harvesting those seeds. Production of the seeds is suitably done by crossing or selfing. Crossing may e.g. be done by means of hand pollination or by employing suitable pollinating insects.

In one embodiment, the invention relates to a method for the production of a *Cichorium* plant, in particular a *Cichorium endivia* plant, exhibiting the reversible genic male sterility trait by using tissue culture.

The invention furthermore relates to a method for the production of a *Cichorium* plant, in particular a *Cichorium endivia* plant, exhibiting the reversible genic male sterility trait by using vegetative reproduction.

In one embodiment, the invention relates to a method for the production of a *Cichorium endivia* plant exhibiting the reversible genic male sterility trait by using a method for genetic modification to introgress in particular dominantly acting transgenes that cause the said trait into the *Cichorium endivia* plant, for example by means of RNAi, amiRNA or antisense, or dominant-negative versions of a target gene, or through mutation. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. The plant may also be genetically modified by mutation of a target gene to exhibit the male sterility trait of the invention.

The invention also relates to a breeding method for the development of *Cichorium* plants, in particular *Cichorium endivia* plants that exhibit the reversible genic male sterility trait wherein germplasm which may comprise said trait is used. Representative seed of said plant which may comprise the genetic determinant and being representative for the germplasm was deposited with the NCIMB under deposit number NCIMB 42092.

In a further embodiment the invention relates to a method for the production of a *Cichorium* plant, in particular a *Cichorium endivia* plant, exhibiting the reversible genic male sterility trait wherein progeny or propagation material of a plant which may comprise the genetic determinant conferring said trait is used as a source to introgress the said trait into another *Cichorium* plant, in particular another *Cichorium endivia* plant. Representative seed of said plant which may comprise the genetic determinant was deposited under deposit number NCIMB 42092.

The invention provides preferably a *Cichorium* plant, in particular a *Cichorium endivia* plant, exhibiting the reversible genic male sterility trait, which plant is obtainable by any of the methods herein described and/or familiar to the skilled person.

This invention also relates to the use of *Cichorium* plants exhibiting a reversible genic male sterility trait as a female parent for the creation of hybrid *Cichorium* seeds. The fact that *Cichorium* plants of the invention are unable to self-fertilise due to male sterility (if they are not rendered male-fertile by the application of jasmonic acid and/or one or more jasmonic acid derivatives, in particular methyl jasmonate) makes it possible to efficiently use *Cichorium* plants of the invention as female parents for the efficient creation of hybrid *Cichorium* plants, using pollen from other *Cichorium* plants. Pollination of the plants of the invention may e.g. be achieved by means of manual pollination, or by employing suitable pollinating insects, such as bumblebees, flies or bees, and placing reversible genic male sterile *Cichorium* plants of the invention alongside male-fertile *Cichorium* plants that will function as father plants of the hybrid *Cichorium* seeds, by providing functional pollen grains for a successful fertilisation of the reversible genic male sterile *Cichorium* plants of the invention. This invention further relates to hybrid *Cichorium* seeds, obtainable by the use of *Cichorium* plants exhibiting a reversible genic male sterility trait as a female parent.

This invention also relates to a food product, which may comprise edible parts of plants of the Compositae family, optionally in processed form, wherein the plants comprise the genetic determinant underlying the reversible genic male sterility trait of the invention. These edible parts may be leaves (e.g. in case of lettuce, endive, witloof and radicchio), or seeds (e.g. in the case of sunflower), or flowers (e.g. in the case of artichoke). The food products are preferably derived from lettuce and endive.

The word "trait" in the context of this application refers to the phenotype of the plant. In particular, the word "trait" refers to the trait of the invention, more in particular to the reversible genic male sterility trait. The term "genetic determinant" is used for the genetic information in the genome of the plant that causes the trait of the invention. When a plant shows the trait of the invention, its genome may comprise the genetic determinant causing the trait of the invention. The plant thus has the genetic determinant of the invention. The term "genetic determinant" as used herein encompasses a gene or allele. These terms are used interchangeably. A genetic determinant may be identified by the use of a molecular marker. A genetic determinant may alternatively be identified by the position on a genetic map, or by indication of the location on a linkage group or chromosome. When a genetic determinant is no longer linked to a specific molecular marker, but its position on a chromosome as defined on a genetic map is unaltered, this genetic determinant is still the same as when it was linked to the molecular marker. The genetic trait that it confers is therefore also still the same.

The "genetic trait" is the trait or characteristic that is conferred by the genetic determinant. The genetic trait may be identified phenotypically. However, also plant stages for which no phenotypic assay may be performed do carry the genetic information that leads to the genetic trait. "Trait" or "phenotypic trait" may be used instead of "genetic trait".

It is clear that the parent that provides the trait of the invention is not necessarily a plant grown directly from the deposited seeds. The parent may also be a progeny plant from the seed or a progeny plant from seeds that are identified to have the trait of the invention by other means.

This invention also relates to the use of plants of the Compositae family which may comprise the genetic determinant underlying the reversible genic male sterility trait of the invention, or of plants produced from the seed of such plants or from propagation material of such plants, as germplasm in a breeding program for the development of Compositae plants exhibiting a reversible genic male sterility that may be reversed by the application of jasmonic acid and/or one or more jasmonic acid derivatives, in particular methyl jasmonate.

Seeds of *Lactuca sativa* which may comprise a genetic determinant of the invention which leads to reversible genic male sterility that may be reversed by the application of jasmonic acid and/or one or more jasmonic acid derivatives, in particular methyl jasmonate, were deposited with NCIMB Ltd, Ferguson Building, Craibstone 5 Estate, Bucksburn, Aberdeen AB21 9YA, UK on Oct. 8, 2012 under deposit accession number NCIMB 42060. All seeds of this deposit comprise the genetic determinant of the invention in a homozygous state.

Seeds of *Cichorium endivia* which may comprise a genetic determinant of the invention which leads to reversible genic male sterility that may be reversed by the application of jasmonic acid and/or one or more jasmonic acid derivatives, in particular methyl jasmonate, were deposited with NCIMB Ltd, Ferguson Building, Craibstone 5 Estate, Bucksburn, Aberdeen AB21 9YA, UK on 21 Dec. 2012 under deposit accession number NCIMB 42092. About 50% of the seeds of this deposit comprise the genetic determinant of the invention in a homozygous state, and about 50% of the seeds of this deposit comprise the genetic determinant of the invention in a heterozygous state.

Sequence Information

SEQ ID No.1: Genetic SNP marker that is able to identify the presence of the genetic determinant that underlies the trait of the invention in *Lactuca sativa* plants grown from seeds that are deposited under accession number NCIMB 42060. A genomic fragment of the lettuce OPR3 gene is presented, wherein the position of the SNP which may comprise a change from C to T [C/T] is indicated as a T in bold and underlined. This SNP is present in plants grown from seeds of the said deposit.

```
atggctgaaacaccgccgtctgccgacaatccaactctcttttctccatt
caagatgggcaagtttaatctctctcacaggtccgttgtttctatcctttt
cttctcttcactttctaatcataaatccgtccccctataaaagtccttc
agattttgagcttgatccagtcttgaccgatcactataccgtgttttggt
tgtagggtggtgttagctccgatgacgcggtgtagggcgttaaatagcat
accgaatcaagctctggtggagtattacaggcagagagcaaccgccggtg
ggtttctcatcacggaggggacaatgatctctcctacctccgccgggtaa
tttcgctattcctttgttcttcaagggtgttttagtaaatcaacattcc
aacataattcaccgggacaaaccatataaaaccgccacgtggcaattctt
agttccttacatagtgctttgtgggacctgcagtatagactattattaaa
gtcacaccattattaaagtcacattctctttataaccactttataaagtc
tttataactaaaaaatgtgtttttttcgttgtactttatagttagattag
atgcataatgtggatcttatgaaccattaaacaatgatacaagctacttg
tgttctaaagttaaagatgccatttgattcttaatttaaaaaacccatt
tggtttaggaatacccctttattcatcgatcattataaagcccaaattaa
cgatctttctggtaaaaaaaaacccaatttggtgatcaggttccctcacg
taccaggtatatttaatcaagaacaagttgaagcttggaagaaagtcgtg
gatgcagttcatgaaaaaggcgctgtgatcttttgtTaattatggcatgt
cggcagagcatcccaccaaggtacgctttcttccatctaaaagtctcaaa
atctcaacattttgattttgaacctaaattcgaatcgaaagtgatcatt
gtgttgaacaaacagtatatcaacctaatggggttgcaccaatatcatct
acaagcaaacccatatcgaaaaaatggagaattttaatgcccgatgggac
ccacgctcaatatccaaaccctcgaccactcgctacccatgaaataccag
aggtggtggaagactatcgtctggcagcaattaacgccattgaagcaggt
tttgatggaatcgagattcacggagcccatggttatcttctcgatcaatt
catgaaagatggcatcaataatcgaaccgatgaatatggtggatctttag
caaaccgatgcaaattcttactgaaagtggtgaaatcgatagctacagcc
attggtgcagataaagtcggtgttagaatctcaccagctattgaccattt
agacgccatggattctgacccacgtagcttagggcttgaagtaattgaaa
gactgaataaacttcaggttgaattagggtcaaagttgacttatcttcat
gtgactcaaccaaggtacacggcttatggtcaaacagaagctggaagcca
tggaagtgaagaggaagttgctgagttgatgaagatatggagaagggcat
ttatgggaactttttgtttgtagtggtgggtatactagagagcttgggatt
gaagctgtggctaaaggggatgctgatttggtggcttatggaaggctttt
tatatcgaatccggatttggttttgagactcaaggttaatgcacctttga
ataggtatgttagggctagttttttatacacatgatcctgttgtagggtac
actgattacccttcacttgagaA
```

SEQ ID No. 2: Genetic SNP marker that is able to identify the presence of the genetic determinant that underlies the trait of the invention in *Cichorium endivia* plants grown from seeds that are deposited under NCIMB number 42092. A genomic fragment of the endive OPR3 gene is presented, wherein the position of the SNP which may comprise a change from C to A [C/A] is indicated as A in bold and underlined. The SNP is present in plants grown from seeds of the said deposit.

```
TCAACATCCAGATCTCCGATCCCAAGCAAATAATGGCTGAAACGACGCCG
TCTGCCGACAATCCAACCCTCTTTTCTCCGTACAAGATGGGCAAGTTCAA
TCTCTCTCACAGGGTGATCAGTTACTTTACTTCGATCCATTGTTCTCGCA
GCTTTCTGATCATACTTCATTCCCCCAGCAAAATAATTCAGAATTTGACC
TTGATCCAATTCTGTTTTTAATTCTTTTACCGATTAGTTCACCGTGTTTT
GGTTGTAGGGTGGTGTTAGCTCAGATGACGAGATGCAGG
```

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Reversible Male Sterility in Lettuce

A mutant lettuce plant (*Lactuca sativa*), having a mutated version of the OPR3 gene, was obtained by means of chemical mutagenesis and subsequent TILLING screening of about 3,000 M2 plants. DNA sequencing revealed the presence of a C to T mutation (CAA to TAA) in one M2 plant, leading at the protein level to the conversion of a Glutamine to a premature stop codon at position 107, and hence to the presumed expression of a truncated version of the OPR3 protein in this mutant plant.

Phenotypically this mutant lettuce plant was indistinguishable from wild type lettuce plants, when the mutation was present in a heterozygous state. However, when the plant was self-pollinated and allowed to produce seeds, the homozygous mutant plants of the next generation showed complete male sterility. The few pollen grains that developed in such homozygous mutants were not functional. The homozygous mutant plants did not set seed when allowed to self-pollinate, but when used as the female parent in a cross, the plants were able to set seed, which demonstrated that their female fertility was not impaired. In this manner the mutation could be maintained in subsequent generations through screening of progeny plants of the selfing of a heterozygous mutant plant with a molecular marker designed to identify the presence of the causal mutation, SEQ ID No. 1, even though the homozygous mutant plants were male sterile and failed to set seed through self-pollination.

Surprisingly, it was observed that spraying young flower buds with a 200 μM (0.2 mM) methyl jasmonate (MeJA) aqueous solution (in water plus 0.025% Zipper surfactant) was sufficient to restore male fertility in these homozygous mutants. From the early bolting stage the inflorescences were sprayed 5 times per week, for a total of 3 weeks. In contrast to mock-treated control plants—that were sprayed with an aqueous solution of 0.025% Zipper surfactant—the MeJA treated plants produced seeds in a subset of their flowers, being the flowers that had received an effective MeJA dose at the appropriate developmental stage (FIG. 1).

The seeds that were produced by the homozygous mutant plants treated with MeJA were all homozygous for the mutation, as could be demonstrated by use of a molecular marker detecting the causal mutation (SEQ ID No. 1).

Example 2

Transfer of the Reversible Male Sterility Trait to Another Lettuce Plant

Lettuce plants of the invention (of the deposit, NCIMB 42060) were crossed with wild type (WT) lettuce plants, which do not carry the trait of the invention. The resulting F1 plants from this cross had the same phenotype as the WT plant, i.e. they displayed normal fertility. Nevertheless, the presence of the trait of the invention in a heterozygous state could be detected in all F1 plants by means of a molecular marker. The Single Nucleotide Polymorphism (SNP) that can be used for this purpose is presented as SEQ ID No. 1. This molecular marker can be used to identify the presence of the genetic determinant that underlies the trait of the invention in lettuce plants grown from seeds as deposited under NCIMB number 42060.

In the F2 generation the trait of the invention segregated in a manner that corresponds with a monogenic recessive inheritance. The trait of the invention could be introduced into a wild type lettuce plant by crossing the wild type plant with a plant of the invention and selecting for the desired phenotype, by selection on male sterility and/or the presence of the molecular marker in a homozygous state. The latter method of detection has the advantage that plants of the invention can be identified at a young developmental stage, long before they start flowering. This enables the confident selection of desired plants (carrying the trait of the invention) at the seedling stage, which allows for a more efficient use of plant growth facilities.

The wild type lettuce plant into which the trait of the invention can be introduced can be a lettuce plant of any leaf type, any form or any colour.

In the F2 generation the male sterility trait was also reversible. The addition of jasmonic acid and/or one or more jasmonic acid derivatives, in particular methyl jasmonate, was sufficient to restore male fertility, as described in Example 1.

Example 3

Reversible Male Sterility in Endive

A mutant endive plant (*Cichorium endivia*), having a mutated version of the OPR3 gene, was obtained by means of chemical mutagenesis and subsequent TILLING screening of about 10,000 M2 plants. DNA sequencing revealed the presence of a C to A mutation in exon 2 (CCG to CAG) in one M2 plant, leading at the protein level to a Proline to Glutamine amino acid change at position 76.

Phenotypically this mutant endive plant was indistinguishable from wild type endive plants, when the mutation was present in a heterozygous state. However, when the plant was self-pollinated and allowed to produce seeds, the homozygous mutant plants of the next generation showed male sterility, along with a pale flower colour (almost white, compared to the blue colour of wild type flowers of this endive line). The pollen grains that developed in such homozygous mutants were unable to germinate and therefore dysfunctional. When used as the female parent in a cross, the plants were able to set seed, which demonstrated that their female fertility was not impaired. In this manner the mutation could be maintained in subsequent generations, even though the homozygous mutant plants were male sterile and failed to set seed through self-pollination.

Surprisingly, it was observed that spraying young flower buds on a daily basis—throughout the entire flowering stage of the plant, which lasted about 3.5 months—with a MeJA solution had a dramatic effect on the mutant flowers that developed from the treated flower buds (an aqueous solution of 200 μM (0.2 mM) MeJA with 0.025% Zipper surfactant). Instead of developing into flowers with a pale colour, as was the case for untreated or mock-treated flower buds (treated with an aqueous solution of 0.025% Zipper surfactant), the treated flower buds developed into blue flowers. Blue was the wild type flower colour in this endive background. In addition, the flowers that developed from MeJA-treated flower buds produced viable, functional pollen and were able to set seed through self-pollination, whereas control plants sprayed with an aqueous solution of 0.025% Zipper surfactant remained male sterile and hence devoid of seeds.

Other application methods (other than spraying) of jasmonic acid and/or one or more jasmonic acid derivatives, in particular methyl jasmonate, had comparable effects, such as "painting" a MeJA solution onto the surface of young flower buds with a fine brush.

This experiment demonstrated that the male sterility that was caused by the opr3 mutation in endive could be overcome by the application of MeJA. The seeds that were produced by selfing of the homozygous mutant plants treated with MeJA were all homozygous for the mutation. Jasmonic acid or other derivatives thereof had the same effect.

Figure 2:
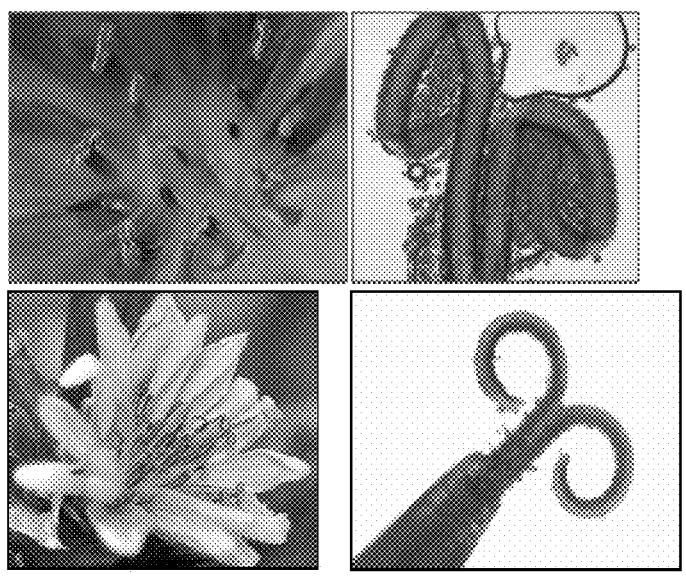
FIG. 2: Reversible male sterility in endive. Panel A shows the flower and stamens of a wild-type endive plant (upper 2 pictures), which has a blue colour and normal pollen production, as compared to a typical flower of a reversible genic male sterile endive plant of the invention, which has a pale flower colour and less pollen production (lower 2 pictures). The pollen grains produced by the endive plants of the invention were not functional. Panel B illustrates the effect of treatment with jasmonic acid and/or jasmonic acid derivatives on the fertility of a reversible genic male sterile endive plant of the invention. The left-hand picture shows an untreated flower of a plant of the invention, which is white in colour and male-sterile. The right-hand picture shows a plant of the invention with in the centre a flower that has been treated with methyl jasmonate at an early stage of its development. Its colour has changed to blue, and it has become male-fertile.
Figure 2:

The presence of the mutation could be detected by means of molecular markers (the SNP marker that can be used for this purpose is presented as SEQ ID No. 2), and in flowering plants one could also use the flower colour as a visual marker. Homozygous mutants have very pale (almost white) flowers than the flowers of wild type and heterozygous plants, which are blue (FIG. 2).

Example 4

Transfer of the Reversible Male Sterility Trait to Another *Cichorium* Plant The deposited endive seeds harbouring the trait of the invention (deposited as NCIMB number 42092) have been produced by allowing endive plants homozygous for the reversible male sterility trait to be pollinated by bumblebees, with pollen from endive plants heterozygous for the reversible male sterility trait. The latter plants are fully male fertile. Of the seeds resulting from this cross about 50% were homozygous for the trait of the invention, and about 50% were heterozygous for the said trait.

Endive plants of the invention were crossed with wild type (WT) endive plants, which do not carry the trait of the invention. Plants grown from seeds of the deposit were first selected (phenotypically on the basis of male sterility and/or a pale flower colour, and/or on the presence of the causal SNP mutation in the OPR3 gene in a homozygous state), to ensure that the trait of the invention would be transferred to the F1 generation in 100% of the cases. Alternatively, this selection can be done in the F2 generation, although this is less efficient.

The F1 plants resulting from this cross had the same phenotype as the wild type plant, i.e. they displayed normal fertility and a normal, blue flower colour. Nevertheless, the presence of the trait of the invention in a heterozygous state could be detected by means of a molecular marker. The SNP that can be used for this purpose is presented as SEQ ID No. 2. This molecular marker can be used to identify the presence of the genetic determinant that underlies the trait of the invention in endive plants grown from seeds as deposited under NCIMB number 42092.

In the F2 generation the trait of the invention segregated in a manner that corresponds with a monogenic recessive inheritance. The trait of the invention could be introduced into a wild type endive plant by crossing the wild type endive plant with an endive plant of the invention and after selfing selecting for the desired phenotype in the F2 generation, for example by selection on male sterility and/or the presence of the molecular marker in a homozygous state. The latter method of detection has the advantage that plants of the invention can be identified at a young developmental stage, long before they start flowering.

In the F2 generation the male sterility trait was also reversible. The addition of jasmonic acid and/or one or more jasmonic acid derivatives, in particular methyl jasmonate, was sufficient to restore male fertility, as described in Example 3.

In a similar manner the trait of the invention can also be introduced into e.g. witloof or radicchio plants (*Cichorium intybus*).

The invention is further described by the following numbered paragraphs:

1. Plant of the Compositae family exhibiting a reversible genic male sterility trait, characterised in that the genic male sterility is caused by a reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase, or their functional homologues.

2. Plant of paragraph 1, wherein the male sterility can be reversed by the application of jasmonic acid and/or one or more jasmonic acid derivatives, in particular methyl jasmonate.

3. Plant of paragraph 1 or 2, wherein the interfering with the one or more target genes consists of preventing transcription thereof.

4. Plant of paragraph 3, wherein transcription is preferably prevented by means of RNA oligonucleotides, DNA oligonucleotides or RNAi molecules directed against the target gene promoter, or wherein transcription is preferably prevented by means of the expression of a negatively acting transcription factor acting on the target gene promoter.

5. Plant of paragraph 1 or 2, wherein the interfering with the one or more target genes consists of destabilising the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides, or wherein the interfering with the one or more target genes consists of inhibiting the target gene expression product, preferably by means of the expression product(s) of one or more dominant negative nucleic acid constructs, or preferably by means of one or more chemical compounds.

6. Plant of paragraph 1 or 2, wherein the interfering with the one or more target genes consists of the introduction of one or more mutations into the target gene, leading to perturbation of its biological function, and wherein the one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements, and/or wherein the one or more mutations are introduced specifically by means of homologous recombination or oligonucleotide-based mutation induction.

7. Plant of any one of the paragraphs 1-6, wherein the plant is a plant of the genus *Lactuca*.

8. Plant of paragraph 7, wherein the plant is a plant of the species *Lactuca sativa*, and wherein the male sterility trait is caused by a genetic determinant, which is as present in the genome of plants grown from seed of which a representative sample was deposited with the NCIMB under accession number NCIMB 42060, in which the presence of the said genetic determinant can be identified by a molecular marker characterised by SEQ ID No. 1.

9. Plant of the Compositae family of any one of the paragraphs 1-6, wherein the plant is a plant of the genus *Cichorium*.

10. Plant of paragraph 9, wherein the male sterility trait is caused by a genetic determinant, which is as present in the genome of plants grown from seed of which a representative sample was deposited with the NCIMB under accession number NCIMB 42092, in which the presence of the said genetic determinant can be identified by a molecular marker characterised by SEQ ID No. 2.

11. Plant of paragraphs 9-10, wherein the homozygous presence of the genetic determinant underlying the male sterility trait can be identified by a pale flower colour, when compared to plants not having the said genetic determinant, or to plants in which the said genetic determinant is present in a heterozygous state.

12. Use of the plant of paragraphs 7-8 as a female parent for the creation of hybrid *Lactuca* seeds.

13. Use of the plant of paragraphs 9-11 as a female parent for the creation of hybrid *Cichorium* seeds.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Lactuca sativa* plant comprising a reversible genic male sterility trait, wherein the genic male sterility trait is caused by a genetic determinant, which is as present in the genome of plants grown from seed of which a representative sample was deposited with the NCIMB under accession number 42060, wherein said genetic determinant is SEQ ID No: 1.

2. A method of creating hybrid *Lactuca* seeds comprising pollinating the plant of claim 1 with a pollen of a male-fertile *Lactuca sativa* plant.

* * * * *